United States Patent [19]

Wang

[11] Patent Number: 5,606,006
[45] Date of Patent: Feb. 25, 1997

[54] TRISEPOXY RESIN COMPOSITIONS

[75] Inventor: Pen-Chung Wang, Houston, Tex.

[73] Assignee: Shell Oil Company, Houston, Tex.

[21] Appl. No.: 629,310

[22] Filed: Apr. 8, 1996

[51] Int. Cl.$^6$ .................................................... C08G 59/00
[52] U.S. Cl. .............................. 528/87; 528/96; 528/97; 528/98; 549/517; 549/519; 549/545
[58] Field of Search .................. 548/517, 519, 548/545; 528/87, 96, 97, 98

[56] References Cited

U.S. PATENT DOCUMENTS 4,113,495  9/1978  Shishido et al. ..................... 96/100 R
4,672,101  6/1987  Wang et al. ........................... 528/96

FOREIGN PATENT DOCUMENTS 2085405   6/1993   Canada .
01289947  11/1989  Japan .
03074426  3/1991   Japan .
05034912  2/1993   Japan .

Primary Examiner—Melvyn I. Marquis
Assistant Examiner—Randy Gulakowski

[57] ABSTRACT

Cure of a novel trisepoxy resin-based composition provides a thermoset having high Tg, low dielectric constant, low water absorption and good flexural strength.

8 Claims, No Drawings

TRISEPOXY RESIN COMPOSITIONS

FIELD OF INVENTION

This invention relates to trisepoxy resin compositions. In one aspect, the invention relates to high-Tg, low water absorbent epoxy resin compositions which can be fabricated into high-performance composites.

BACKGROUND OF THE INVENTION

Epoxy resins for high-performance applications such as aerospace and electrical molding, composites, or laminates have been developed which meet the high-temperature requirements of such applications. For example, epoxy resins based on spirodilactams have high glass transition temperatures (Tg) but suffer from excessively high water absorption for high-performance use. Increasingly, an additional requirement for epoxy resins is a viscosity profile which permits solventless processing of the resins. Epoxy resin compositions based on commercial epoxy resins such as epoxy resins based on diglycidyl ethers of bisphenol-A have low glass transition temperatures.

It is therefore an object of the invention to provide an epoxy resin composition which exhibits a cured Tg above 200° C., low water absorption and processability in the melt useful for laminating, molding and/or compositing.

SUMMARY OF THE INVENTION

According to the invention, a trisepoxy resin composition is provided, a trisepoxy resin having the structural formula

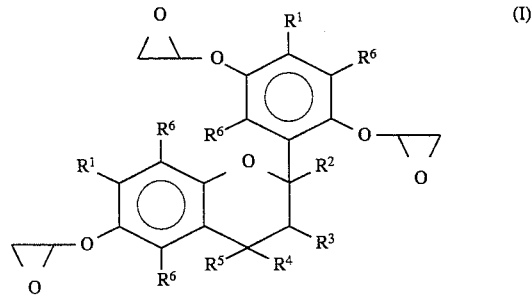

in which $R^1$s and $R^6$s are independently a hydrogen atom or a $C_{1-20}$ alkyl group, provided $R^1$s do not simultaneously represent hydrogen atoms, $R^2$ is methyl or together with $R^3$ form a fused ring, $R^3$ is hydrogen atom or together with $R^2$ form a fused ring, $R^4$ and $R^5$ are independently a $C_{1-6}$ alkyl or together form a spiro-ring. Further, a composition is provided comprising (a) the trisepoxy resin of formula (I) and (b) a curing agent for the epoxy resin. According to one embodiment of the invention, such a trisepoxy resin composition containing a polyamine or phenolic curing agent is employed to prepare electrical laminates, structural composites and molding compounds.

DETAILED DESCRIPTION OF THE INVENTION

It has been found that a certain trisepoxy resin can be prepared having a Tg of above 200° C. and a water absorption of less than 4.0% (93° C., 2 wks) when cured with a curing agent for epoxy resins, particularly, aromatic amines, cyanamides and phenolic curing agents, useful for electrical laminates, structural composites and molding compounds.

The trisepoxy resin can be prepared by reacting the precursor trisphenol (Formula II described below) with an epihalohydrin such as epichlorohydrin in the presence of a caustic such as aqueous sodium hydroxide. The reaction can be carried out at a temperature within the range of about 20° to about 120° C., preferably about 50° to about 100° C. The reaction is preferably carried out in a solvent such as isopropyl alcohol. By-product salts can be separated by filtration, and the solvent and excess epihalohydrin removed by evaporation under reduced pressure.

The precursor bisphenols can be described by the formulas

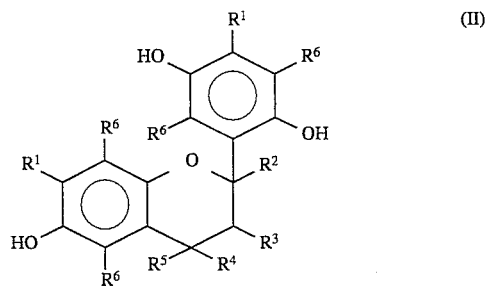

in which $R^1$s and $R^6$s are independently a hydrogen atom or a $C_{1-20}$ alkyl group or alkoxy group, provided $R^1$s do not simultaneously represent hydrogen atoms, $R^2$ is methyl or together with $R^3$ form a fused ring, $R^3$ is hydrogen atom or together with $R^2$ form a fused ring, $R^4$ and $R^5$ are independently a $C_{1-6}$ alkyl or together form a spiro-ring. Such trisphenols can be prepared by the condensation reaction of ketones, preferably having 1 to 6 carbon atoms, such as acetone, cyclohexanone, and/or methylethyl ketone with hydroquinones. Hydroquinones can be substituted with inert substituents such as those corresponding to $R^1$s or unsubstituted. Most of hydroquinones having substituents corresponding to $R^1$s are commercially available. Examples of hydroquinones include, hydroquinone, methylhydroquinone, t-butylhydroquinone, allylhydroquinone, toluylhydroquinone, phenylhydroquinone, and methoxy hydroquinone.

The reaction is most efficiently carried out in the presence of an acid such as glacial acetic acid, concentrated hydrochloric acid or sulfuric acid at a temperature within the range of about 0° to about 70° C., preferably about 20° to about 60° C. The reaction is continued until the desired degree of reaction has been completed, usually for a time within the range of about 30 minutes to about 16 days, preferably until sufficient crystals are precipitated. Methods for preparing some of the trisphenols reactants are described in U.S. Pat. No. 4,113,495 which is herein incorporated by reference. The trisphenols produced are typically recovered prior to preparing the trisepoxy resin.

The trisepoxy resins are preferably used in combination with an optional halogenated phenolic compound and a curing agent effective to cure the epoxy resin to a thermoset material having a glass transition temperature greater than 200° C. and a moisture absorption less than 4.0% (93° C., 2 wks) and having good flexural strength (greater than 10). Preferable halogenated phenolic compound can be any phenolic compound substituted with a halogen such as bromine (e.g., tetrabromobisphenol-A). Preferable curing agents include, for example, cyanamides such as dicyandiamide, aromatic amines such as diaminodiphenyl sulfone, isophoronediamine and 1,3-bis(aminomethyl)-benzene, and phenolic compounds such as hisphenol-A, hisphenol-F, o-cresol and phenolic novolacs. When used in solventless lamination, the preferred curing agent is a polyhydric phenol such as an o-cresol or phenolic novolac used in combination with an accelerator such as an imidazole.

The trisepoxy resin can be used in combination with other epoxy resins such as diglycidyl ethers of bisphenol-A and F, diglycidyl ethers of biphenols, tetraglycidyl ethers of the tetraphenol of ethane, and polyglycidyl ethers of aromatic amines, spirodilactam-based epoxy resins, for example.

The invention epoxy resin compositions are cured by exposure of the trisepoxy resin, curing agent and optionally halogenated phenolic compound formulation to elevated temperature within the range of about 150° to about 250° C. for a time generally greater than about 2 hours. Optimum properties in the cured resin can be achieved by a staged heating process employing higher temperature in each stage. The trisepoxy resins can be co-cured with other epoxy resins and other thermosettable resins such as bismaleimides and cyanate esters for high-temperature electrical composites or laminates. The trisepoxy resin of the invention is readily processable as a melt at its curing temperature and lower to a typical melt processing temperature of 120° C.

The invention epoxy resins are useful, for example, in electrical laminates, structural composites and molding compounds. The trisepoxy resin or the curable trisepoxy resin composition of the invention can be further mixed at any stage before cure, with usual modifiers such as extenders, fillers, reinforcing agents, pigments, dyestuffs, organic solvents, plasticizers, thixotropic agents, flame-retardants and flow control agents.

An electrical component can be encapsulated by injecting the curable epoxy resin composition containing a trisepoxy resin as described above and a phenolic curing agent, optionally halogenated phenolic compound and a filler in a die with the component to be encapsulated and then curing the resin.

In a prepregging process, a fibrous substrate, usually woven glass, is impregnated with a solventless formulation or formulation with solvent (e.g., ketones) containing a trisepoxy resin as described above, a halogenated phenolic compound, optionally a polyphenolic curing agent and optionally a cure accelerator, and the impregnated substrate is passed to an oven maintained at a temperature effective to partially cure the epoxy resin. In a solvent-borne process a conventional process can be used. In a specific embodiment of the solventless lamination process, the prepreg is prepared in a process involving depositing the solventless trisepoxy-based epoxy resin formulation in the melt onto a rotating roller, passing a fibrous web in countercurrent contact with the resin formulation on the rotating roller so as to transfer the resin formulation into the fibrous web, and passing the resin-containing web to a heating zone to partially cure the resin and form a prepreg comprising the fibrous web and the partially-cured resin. The prepreg can be shaped into a desired shape and cured to obtain a laminate.

The prepregs or molds are cured under effective conditions to provide a molded or laminated composition (containing a glass substrate or an electrical component and cured trisepoxy resin composition) having a glass transition temperature (Tg) of greater than 200° C. and a water absorption of less than 0.2% (15 psi steam, 30 min.).

ILLUSTRATIVE EMBODIMENT

The following illustrative embodiments describe the novel trisepoxy resin composition of the invention and are provided for illustrative purposes and are not meant as limiting the invention.

EXAMPLE 1

62.0 grams of methylhydroquinone and 87.0 grams of acetone were added to a mixed solution of 170 ml of concentrated HCl (12N) and 300 ml of glacial acetic acid and left for three days at room temperature. The resulting crystals were collected by filtration and washed with $H_2O$ (m.p. 190° C.).

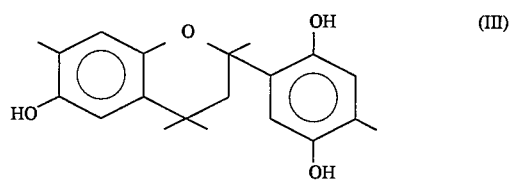

(III)

EXAMPLE 2

A mixture of 173 grams (0.527 moles) of trisphenol from Example 1, 1462 grams (15.81 mole) of epichlorohydrin, 853.7 grams of isopropyl alcohol and 246 grams of water were placed in a 5-liter round-bottom flask equipped with a mechanical stirrer, a condenser and warmed with stirring to 80° C. 758 grams of 20% sodium hydroxide aqueous solution is then added dropwise over a period of 40 minutes. After reaction, excess epichlorohydrin and solvents are removed under reduced pressure to give the corresponding trisepoxy resin (IV) with a melting point 112°–120° C. and weight per epoxy or 186.

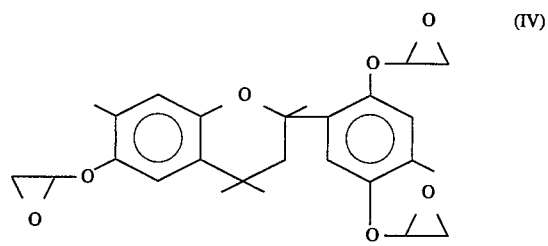

(IV)

EXAMPLE 3

Trisepoxy resin (IV), 46.30 gram was heated with 23.7 grams of HPT-1061 Curing Agent (α,α-4-aminophenyl-p-diisopropenylbenzene from Shell Chemical Co.) at 170° C. for 2 hours, 200° C. for 3 hours, and 220° C. for 2 hours to give a cured material having the physical properties shown in Table 1.

EXAMPLE 4

Trisepoxy resin (IV), 51.13 gram was heated with 18.87 grams of DDS Curing Agent (4-aminophenyl sulfone from Aldrich Chemical Co.) at 170° C. for 2 hours, 200° C. for 3 hours, and 220° C. for 2 hours to give a cured material having the physical properties shown in Table 1.

EXAMPLE 5

62.0 grams of methylhydroquinone (0.5 mole) and 147 grams of cyclohexanone (1.5 mole) were added to a mixed solution of 170 cc HCl and 300 cc acetic acid and left for 3 days at room temperature. The resulting crystals were recrystallized from ethanol to obtain 30.5 grams of colorless needle-like crystals having a melting point of 190° C.

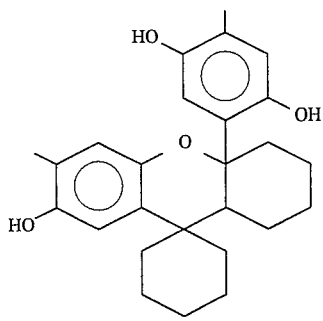

(V)

EXAMPLE 6

A mixture of 50 grams (0.122 mole) of trisphenol from Example 5, 340 grams of epichlorohydrin, and 0.65 grams of ethyltriphenylphosphonium bromide is stirred for 2 hours at 105°–110° C. The contents of the flask are allowed to cool and 35 ml of toluene is added. The pressure in the flask is then reduced to 20–25 mm Hg and the flask heated to 70°–80° C. Then, 31 grams of 50% sodium hydroxide solution is added drop by drop with azeotropic removal of the water. Then, distillation is continued for an additional 60 minutes with circulation of epichlorohydrin. The reaction mixture is cooled and NaCl is removed by suction filtration. The epichlorohydrin solution is washed with water and concentrated under reduced pressure to dryness to five a trisepoxy resin (VI) with melting point of 129°–139° C.

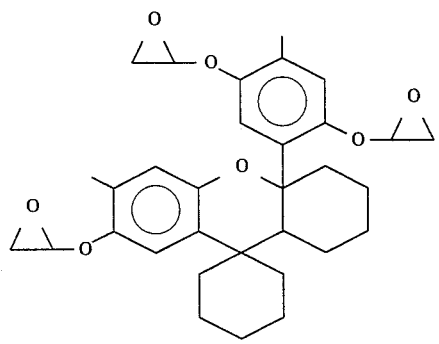

(VI)

It is expected that trisepoxy resin (VI) can be cured with Curing Agents in a similar manner to Examples 3 and 4 above to provide a cured product with a Tg of greater than 250° C. and a water gain of less than 4%.

TABLE 1

| Examples | 3 | 4 |
|---|---|---|
| Tg | | |
| (DSC) | 270 | 290 |
| (DMA) | 280 | 330 |
| Flexural Properties (Dry/RT) | | |
| Strength (ksi) | 16.2 | 17.0 |
| Modulus (ksi) | 393 | 422 |
| Elongation (%) | 6.0% | 5.6% |
| Flexural Properties[1] (Hot/Wet) | | |
| Strength (ksi) | 11.4 | 11.0 |

TABLE 1-continued

| Examples | 3 | 4 |
|---|---|---|
| Modulus (ksi) | 327 | 335 |
| Elongation (%) | 6.1% | 4.8% |
| Modulus Retention (%) (2 weeks at 93° C. water bath) | 83.2% | 80% |
| Fracture Toughness[2] (kg) | 540 | 413 |
| Water Gain (%) | 2.44% | 3.8% |
| Dielectric Constant[3] | 3.75 | 4.18 |

[1]Flexural properties were determined by a method based on ASTM 790.
[2]Fracture toughness was determined using the compact specimen according to ASTM E 399-83.
[3]Dielectric constant was determined at 1 MHz by a method based on ASTM D150.

I claim:

1. A trisepoxy resin having the structural formula

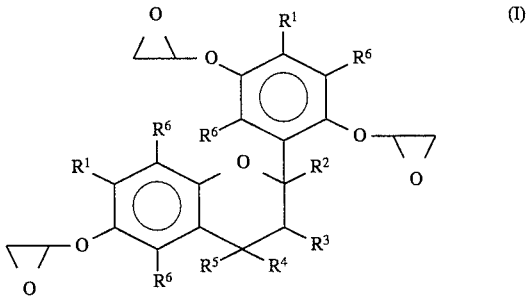

(I)

in which $R^1$s and $R^6$s are independently a hydrogen atom or a $C_{1-20}$ alkyl group, provided $R^1$s do not simultaneously represent hydrogen atoms, $R^2$ is methyl or together with $R^3$ form a fused ring, $R^3$ is hydrogen atom or together with $R^2$ form a fused ring, $R^4$ and $R^5$ are independently a $C_{1-6}$ alkyl or together form a spiro-ring.

2. The trisepoxy resin of claim 1 having the formula:

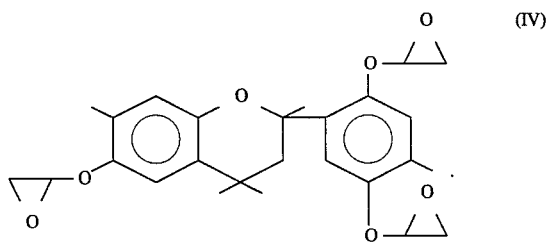

(IV)

3. The trisepoxy resin of claim 1 having the formula:

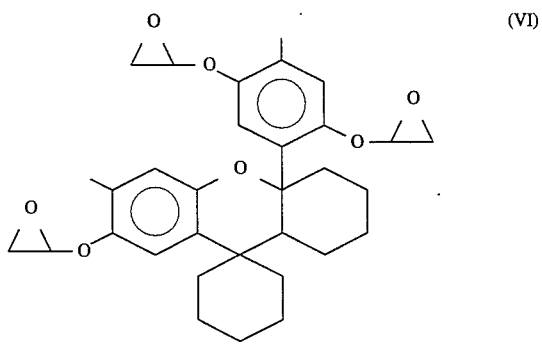

(VI)

4. The trisepoxy resin composition prepared by reacting a trisphenol of the formula:

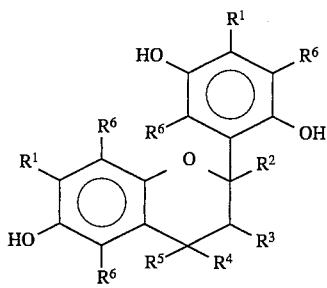

(II)

in which $R^1$s and $R^6$s are independently a hydrogen atom or a $C_{1-20}$ alkyl group or alkoxy group, provided $R^1$s do not simultaneously represent hydrogen atoms, $R^2$ is methyl or together with $R^3$ form a fused ring, $R^3$ is hydrogen atom or together with $R^2$ form a fused ring, $R^4$ and $R^5$ are independently a $C_{1-6}$ alkyl or together form a spiro-ring and an epihalohydrin in the presence of a caustic.

5. The trisepoxy resin composition of claim 4 wherein the trisphenol is prepared by reacting a ketone with a hydroquinone.

6. The trisepoxy resin composition of claim 5 wherein the ketone is selected from the group consisting of acetone, cyclohexanone, methylethyl ketone and diethyl ketone.

7. The trisepoxy resin composition of claim 6 wherein the hydroquinone is selected from the group consisting of hydroquinone, methylhydroquinone, t-butylhydroquinone, allylhydroquinone, toluylhydroquinone, phenylhydroquinone, and methoxy hydroquinone.

8. A method of preparing a trisepoxy resin having a melting point within the range of from about 100° C. to about 150° C. comprising:

(a) reacting a ketone and a hydroquinone in the presence of an acid at a temperature within the range of about 0° to about 70° C. thereby producing a trisphenol;

(b) reacting said trisphenol with an epihalohydrin in the presence of a caustic at a temperature within the range of about 20° to about 120° C. thereby producing a trisepoxy resin;

(c) recovering the trisepoxy resin.

* * * * *